United States Patent
Röchling et al.

(12)

(10) Patent No.: US 6,410,481 B1
(45) Date of Patent: Jun. 25, 2002

(54) WATER-DISPERSIBLE GRANULES OF SUSPOEMULSIONS

(75) Inventors: Hans Röchling, Bad Soden am Taunus; Hans Schumacher, Flörsheim am Main; Joachim Baumgärtner, Frankfurt am Main, all of (DE)

(73) Assignee: Hoechst Aktiengesellschaft, Frankfurt am Main ( * ) Notice: Subject to any disclaimer, the term of this patent is extended or adjusted under 35 U.S.C. 154(b) by 0 days.

(21) Appl. No.: 08/445,165

(22) Filed: May 19, 1995

Related U.S. Application Data

(63) Continuation of application No. 07/973,982, filed on Nov. 6, 1992, now abandoned.

(30) Foreign Application Priority Data

Nov. 8, 1991 (DE) .......................................... 41 36 781

(51) Int. Cl.$^7$ ........................ A01N 25/14; A01N 37/12; A01N 37/34; A01N 43/24; A01N 47/30
(52) U.S. Cl. ........................ 504/144; 504/367; 514/431; 514/521; 514/952
(58) Field of Search ................................. 504/144, 146, 504/116, 367; 71/DIG. 1; 514/431, 521, 952

(56) References Cited

FOREIGN PATENT DOCUMENTS

| EP | 0224845 | | 6/1987 |
|----|---------|---|--------|
| EP | 388867 | * | 9/1990 |
| EP | 0 413 267 | | 2/1991 |
| EP | 0 443 411 | | 8/1991 |
| ZA | 86/9002 | | 11/1986 |
| ZA | 90/2213 | | 3/1990 |
| ZA | 90/6382 | | 8/1990 |
| ZA | 91/1134 | | 2/1991 |

OTHER PUBLICATIONS

The Agrochemicals Handbook, p A0973, The Royal Society of Chemistry, United Kingdom, Aug. 1991.*

* cited by examiner

Primary Examiner—S. Mark Clardy
(74) Attorney, Agent, or Firm—Frommer Lawrence & Haug LLP

(57) ABSTRACT

The invention relates to water-dispersible granules of a pesticidally active main component of sufficiently high melting point, a liquid pesticidal active substance or pesticidal active substance of low melting point and/or which is not sufficiently biologically active in the solid state, in dissolved form, a solvent or solvent mixture with low volatility, and, if appropriate, further additives or adjuvants. The granules are prepared from an aqueous suspoemulsion of the components by removing the water, for example in a fluidized-bed drier. The novel granules are distinguished by an outstanding spontaneous dispersibility and a good biological activity of the formulations prepared from them.

6 Claims, No Drawings

WATER-DISPERSIBLE GRANULES OF SUSPOEMULSIONS

This application is a continuation of application Ser. No. 07/973,982, filed Nov. 6, 1992 now abandonded.

The present invention relates to novel water-dispersible granules of mixtures of active substances for use in crop protection.

Water-dispersible granules (abbreviation: WG) are described in a series of patent applications as an environmentally friendly type of formulation, distinguished by a high degree of safety for the user and during transport and storage. The formulation type of water-dispersible granules is preferably used in the case of solid active substances of relatively high melting point (m.p.>65° C.). In most cases, the starting materials are aqueous dispersions which are spray-dried or granulated in a fluidized bed. Examples are described in EP-A-413,267, EP-A-388,867 and EP-A-224, 845.

WG formulations can also be prepared of liquid active substances, by adsorbing the latter on a suitable carrier (EP-A-443,411).

Difficulties arise when it is intended to prepare a combined formulation of a solid active: substance which can be formulated in the form of an aqueous dispersion (m.p.>65° C.) and of a liquid active substance or a substance of low melting point, and/or when the second active substance (such as, for example, deltamethrin) must be present at the site of action in dissolved form if its best possible biological action is to be achieved.

Uncontrolled crystallization of the active substance of a low melting point during the preparation of the granules and after storage under warm conditions can result in a reduced biological action; agglomerations and the formation of larger particles can lead to blocked screens and jets.

Surprisingly, it has now been found that even suspoemulsions can be granulated by the fluidized-bed process. Suspoemulsions are aqueous dispersions of solids of sufficiently high melting point and in which the solution of a second active substance is emulsified.

The prerequisite for successful granulation of the above-mentioned suspoemulsions is the selection of a solvent for the emulsifiable concentrate which does not evaporate during the granulation process.

The invention therefore relates to water-dispersible granules which contain 10 to 90% by weight, preferably 40 to 85% by weight, of at least one pesticidal active substance of sufficiently high melting point and which can be formulated in the form of an aqueous dispersion, 0.1 to 20% by weight, preferably 0.5 to 10% by weight, of at least one liquid pesticidal active substance pesticidal or active substance of low melting point and/or which is not sufficiently effective in solid form, this pesticidal active substance being in dissolved form, and 0.2 to 20% by weight, preferably 0.5 to 10% by weight, of a solvent or solvent mixture with low volatility.

Preferred granules are those in which the active substance which can be formulated in the form of an aqueous dispersion (m.p.>65° C.) is present in greater amounts based on weight, and the liquid active substance or active substance of low melting point, or active substance which is not sufficiently biologically active in the solid state, is present in smaller amounts.

The active substances are selected from the series of the herbicides, insecticides, fungicides, acaricides, nematicides, pheromones and repellants, preferably from the series of the herbicides and insecticides. If appropriate, the granules contain at least one safener.

Suitable active substances which can be formulated as a dispersion and which are present in the combined formulation as the principal component are, in particular, isoproturon and endosulfan. As liquid active substances or active substances of low melting point, or active substances which are not sufficiently biologically active in the solid state, are preferably employed: fluoroglycofen-ethyl, trifluralin, triazaphos and deltamethrin; particularly preferred are fluoroglycofen-ethyl and deltamethrin.

Only a few solvents do not evaporate, or to a minor extent only, at the high throughputs of heated gas (air or nitrogen/air mixtures) during fluidized-bed granulation. Moreover, the solvents must have a sufficiently great dissolving capacity for the liquid pesticidal active substance, or pesticidal active substance of low melting point or which is not sufficiently active in solid form, and they must be acceptable for use in agriculture. Solvents whose boiling range is above 170° C. (at, or calculated for, atmospheric pressure) are particularly suitable for this purpose.

It has been found that in particular the following solvents have a low volatility as well as good dissolving properties: ®Solvesso 200 (1), butyl diglycol acetate, ®Shellsol RA (2), ®Actrel 400 (3), ®Agsolex 8 (4), ®Agsolex 12 (5), ®Norpar 13 (6), ®Norpar 15 (7), ®Isopar V (8), ®Exsol D 100 (9), ®Shellsol K (10) and ®Shellsol R (11), the composition of which is as follows:

(1) Mixtures of alkylated naphthalenes, boiling range 219–282° C., manufacturer: Exxon.

(2) Mixtures of alkylated benzenes, boiling range 183–312° C., manufacturer: Shell.

(3) High-boiling mixture of aromatics, boiling range 332–355° C., manufacturer: Exxon.

(4) N-Octylpyrrolidone, boiling point (0.3 mm Hg) 100° C., manufacturer: GAF.

(5) N-Dodecylpyrrolidone, boiling point (0.3 mm Hg) 145° C., manufacturer: GAF.

(6) Aliphatic hydrocarbons, boiling range: 228–243° C., manufacturer: Exxon.

(7) Aliphatic hydrocarbons, boiling range: 252–272° C., manufacturer: Exxon.

(8) Aliphatic hydrocarbon, boiling range: 278–305° C., manufacturer: Exxon.

(9) Aliphatic hydrocarbon, boiling range: 233–263° C., manufacturer: Exxon.

(10) Aliphatic hydrocarbon, boiling range: 192–254° C., manufacturer: Shell.

(9) Aromatic hydrocarbon, boiling range: 203–267° C., manufacturer: Shell.

Mixtures of these solvents with each other are also suitable. Butyl diglycol acetate, ®Actrel 400, ®Agsolex 8 and ®Agsolex 12 are particularly useful.

If appropriate, the granules according to the invention additionally contain 1 to 12% by weight, preferably 4 to 8% by weight, of at least one wetting agent, 2 to 15% by weight, preferably 6 to 12% by weight, of at least one dispersant, 0.2 to 5% by weight, preferably 0.8 to 3% by weight, of at least one adhesive, 0.5 to 60% by weight, preferably 0.8 to 20% by weight, of inert substance, depending on active substance content, and 0.5 to 10% by weight, preferably 1 to 5% by weight, of at least one emulsifier.

Examples of wetting and dispersing agents which can be employed for the preparation of the aqueous dispersion of the active substance of high melting point are the following:

Wetting agents: secondary N-alkanesulfonate (for example ®Hostapur SAS, $C_{14}C_{19}$-olefin sulfonate sodium salt (for example ®Hostapur OS), disodium isodecylsulfomono-succinate (for example ®Netzer IS), sodium lauryl sulfate (for example Texapon K12 or Texapon Z), sodium dodecylbenzenesulfonate (for example phenylsulfonate HS90), sodium oleoylmethyl tauride (for example ®Hostapon T), sodium dibutyl-naphthalenesulfonate (for example ®Leonil DB or ®Geropon NK, ®Nekal BX), alkyl diglycol ether sulfate sodium salt (for example ®Genapol LRO), sodium lauryl ether phosphate (for example ®Forlanit P), oxethylated polyarylphenol phosphate, neutralized with triethanol-amine or potassium hydroxide (for example ®Soprophor FL and ®Soprophor FL-K or HOE S3775, Hoechst AG), ethoxylated tributylphenols (for example ®Sapogenat TO80, T110), ethoxylated nonylphenols (for example ®Arkopal N100), isotrideca-nol polyglycol ethers (for example ®Genapol X-080), polymerization products of propylene oxide and: ethylene oxide (for example ®Genapol PF40), bis-mono-phosphate of a propylene oxide/ethylene oxide block copolymer, neutralized with potassium hydroxide (for example HOE S3618 K salt or ®Alkaphos MD12-116).

Dispersants: Ligninsulfonates, such as, for example, ®Vanisperse CB, ®Borresperse CA, ®Ufoxane 3a, ®Ultrazine Na, ®Hansa FE, Na salt of the sulfonated condensation product of formaldehyde with methylphenol such as, for example, ®Rapidamin Reserve C and D; naphthalenesulfonic acid/formaldehyde condensation products such as, for example, ®Dispersogen A; anionic condensation product of m-cresol, nonylphenol, sodium sulfite and formaldehyde, such as, for example, HOE S1494, by Hoechst AG; anionic condensation product of cresol and formaldehyde such as, for example, dispersant SS; potassium salt of an aqueous polycarboxylic acid solution such as, for example ®Dispersant DG; sodium polycarboxylate, such as, for example, ®Sopropon T36; condensed sodium methyl-naphthalenesulfonate, such as, for example, Supragil MNS90; sodium salt or potassium salt of a carboxylic acid copolymer, combined with an anionic dispersant such as, for example, ®Geropon SC211 and ®Geropon SC213.

The following adhesives can be used to improve the stability of the granules:

Starch syrup, dextrose, methylcellulose, carboxymethyl-cellulose (various ®Tylose products), polyethylene glycol products, partially hydroxylated polyvinyl acetate (various ®Mowiol types such as ®Mowiol 3/83), polyvinylpyrrolidone (such as ®Luviskol K30).

The following can be added to the granules as inert substances:

precipitated silicas, pyrogenic silicas, kaolins, aluminum silicates, also calcined aluminum silicate, attapulgite, montmorillonite, calcium magnesium aluminum silicates.

Example of emulsifiers which can be used for preparing the emulsifiable solution of the liquid active substance, or active substance of low melting point, or active substance which is not sufficiently biologically active in the solid state, are the following:

®Calcium dodecylbenzenesulfonate such as, for example, calcium phenyl sulfonate; ethoxylated castor oil such as, for example, ®Emulsogen EL, and ®Emulsogen E1400; ethoxylated tributylphenols such as, for example, ®Sapogenat-T products; ethoxylated nonylphenols such as, for example, ®Arkopal N products; oleyl alcohol polyglycol ethers such as, for example, ®Genapol O products; isotridecanol polyglycol ethers such as, for example, ®Genapol X products; high-molecular-weight block copolymers of propylene oxide and ethylene oxide such as, for example, HOE S1816 (Hoechst AG); tristyrylphenol polyglycol ethers such as, for example, HOE S3474 (Hoechst AG); triethanolamine polyarylphenol polyglycol ether phosphate such as, for example, HOE S3475 (Hoechst AG); n-butanol/propylene oxide block oxalkylate such as, for example, HOE S3510 (Hoechst AG).

Mixtures of substances from the individual groups can be used, but also combinations of substances from the various groups of the wetting agents, dispersants and emulsifiers.

The invention furthermore relates to a process for the preparation of water-dispersible granules, which comprises removing the water from an aqueous suspoemulsion of the granule components, for example in a fluidized-bed drier.

To prepare the combined formulation described, an aqueous dispersion can therefore first be prepared with the main component which melts above 65° C., using suitable wetting agents and dispersants. In a second step, an emulsifiable solution (emulsifiable concentrate, abbreviation: EC) of the liquid active substance, or active substance of low melting point, or active substance which is not sufficiently biologically active in the solid state, is prepared whose emulsifier composition is selected in such a manner that the solution can be emulsified in the dispersion in such a manner that a stable emulsion results.

The invention also relates to the use of these granules for preparing aqueous preparations of pesticidal active substances.

The following preparation examples are intended to illustrate the invention without imposing any restriction.

General information on the assessment and preparation

The spontaneous dispersibility of the granule formulation is assessed using a key from 1 to 4. To this end, 1 g of the granules is first introduced into a 1 l measuring cylinder filled with standardized water (30° C., 342 ppm $CaCO_3$ water hardness). After 1 minute, the measuring cylinder is rotated slowly by 180° C. and returned to the starting position. This procedure is repeated three times. The following scheme is used in the assessment.

Key

1 All granule particles are dispersed. If undispersed granule particles are present, the cylinder is shaken another three times as described 2 minutes after the beginning of the test and assessed as follows:

2 The granules are now dispersed completely.

3 Remains of the granules are not dispersed.

4 Most of the granules are not dispersed.

The suspensibility was defined as such an amount of the preparation (% by weight) which is found in the uppermost nine tenths of the volume of the suspension after a sedimentation time of 30 minutes has elapsed (see CIPAC Handbook Vol. 1 (1970), p. 861).

By wet-screening residue is understood such an amount of substance which remains on a 250 μm, or 71 μm, screen after 10 minutes washing with a defined amount of water. A description of the method can be found in the "Richtlinien für die amtliche Prüfung von Pflanzenschutzmitteln [Guidelines for the Official Testing of Crop Protection Agents], Part III, 2-1/1 (Aug. 1988) of the Biologische Bundesanstalt Braunschweig".

A laboratory spray drier was used for spray-drying smaller amounts, and a laboratory fluidized bed was used for the fluidized-bed granulation of batches up to approximately 400 g of product. A larger fluidized bed was used for batches of up to approximately 15 kg of product.

EXAMPLE 1

Isoproturon+fluoroglycofen-ethyl–75+2.4–WG

First, an aqueous dispersion of the active substance of high melting point is prepared:

| | |
|---|---|
| 308.16 g | isoproturon, 99.0% |
| 38.64 g | ® Rapidamin Reserve C |
| 17.08 g | ® Forlanit P |
| 4.88 g | ® Alkaphos MD-12-116 |
| 4.76 g | ® Mowiol 3/83 |
| 2.04 g | defoamer based on silicone, for example defoamer SE2 |
| 4.44 g | ® Perlite J 206 |
| 380.00 g | drinking water |
| 760.00 g | |

The components are mixed and ground on a bead mill until 50% of the particles have a size of 2–3 μm. Yield: 596 g Then, the emulsifiable solution of the active substance of low melting point is prepared:

| | |
|---|---|
| 7.26 g | fluoroglycofen-ethyl, 88.5% |
| 7.26 g | ® Agsolex 8 |
| 2.83 g | Hoe S 3510 (Hoechst AG) |
| 0.71 g | calcium dodecylbenzenesulfonate |
| 18.06 g | |

The emulsifiable solution is added to the aqueous isoproturon dispersion, with stirring.

Approximately one third of the resulting suspoemulsion is spray-dried; the fine powder obtained is introduced into the laboratory fluidized-bed granulator and granulated by spraying on the remaining suspoemulsion. 246.4 g (89% of theory) of water-dispersible granules of a spontaneous dispersibility of 1 are obtained; suspensibility=98%. On a 71 μm screen, the wet-screening residue is 0.3%, no residue at 250 μm.

The composition of the granules in percent is:

| | |
|---|---|
| 75.76% by weight | isoproturon, 99.0% |
| 2.26% by weight | fluoroglycofen-ethyl, 88.5% |
| 9.50% by weight | ® Rapidamin Reserve C |
| 4.20% by weight | ® Forlanit P |
| 1.20% by weight | ® Alkaphos MD-12-116 |
| 1.17% by weight | ® Mowiol 3/83 |
| 0.50% by weight | defoamer based on silicone, for example defoamer SE2 |
| 1.09% by weight | ® Perlite J 206 |
| 2.26% by weight | ® Agsolex 8 |
| 0.88% by weight | Hoe S 3510 (Hoechst AG) |
| 0.22% by weight | calcium dodecylbenzenesulfonate |
| 0.96% by weight | residual moisture |
| 100.00% by weight | |

For a good biological activity, it is important that the fluoroglycofen-ethyl in the finished granules is in dissolved form. The content of solvent ®Agsolex 8 in the isoproturon+fluoroglycofen-ethyl WG was analyzed: it was 2.14% by weight. The formulation has a good biological activity.

EXAMPLE 2

Following the description of Preparation Example 1, granules of the following composition are prepared:

| | |
|---|---|
| 75.76% by weight of | isoproturon, 99.0% |
| 2.26% by weight of | fluoroglycofen-ethyl, 88.5% |
| 1.09% by weight of | ® Perlite J 206 |
| 9.00% by weight of | ® Genamin Reserve C |
| 3.29% by weight of | ® Genapol Pf40 |
| 1.20% by weight of | Hoe S 3775 (Hoechst AG) |
| 1.17% by weight of | ® Luviskol K30 |
| 0.50% by weight of | defoamer based on silicone, for example defoamer SE2 |
| 0.96% by weight of | residual moisture |
| 3.39% by weight of | ® Agsolex 12 |
| 0.28% by weight of | calcium dodecylbenzenesulfonate |
| 1.10% by weight of | Hoe S 3510 (Hoechst AG) |

Analysis of the ®Agsolex 12 content in the finished granules gave 3.4% by weight; the biological activity is good.

EXAMPLE 3

Following the procedure of Preparation Example 1, granules of the following composition are prepared:

| | |
|---|---|
| 60.30% by weight of | isoproturon, 99.0% |
| 1.69% by weight of | fluoroglycofen-ethyl, 88.5% |
| 9.00% by weight of | ® Genamin Reserve C |
| 3.30% by weight of | ® Genapol Pf40 |
| 1.20% by weight of | Hoe S 3775 (Hoechst AG) |

-continued

| | |
|---|---|
| 1.17% by weight of | ® Luviskol K30 |
| 0.50% by weight of | defoamer based on silicone, for example defoamer SE2 |
| 18.30% by weight of | Kaolin 1777 |
| 0.50% by weight of | residual moisture |
| 0.47% by weight of | ® Emulsogen EL 400 |
| 0.10% by weight of | calcium dodecylbenzenesulfonate |
| 0.93% by weight of | ® Sapogenat T 180 |
| 2.54% by weight of | ® Actrel 400 |

The finished granules contain 2.5% by weight of ®Actrel 400; the biological activity is good.

EXAMPLE 4

Preparation of isoproturon+fluoroglycofen-ethyl granules without using solvent for fluoroglycofen-ethyl.

| | |
|---|---|
| 3409.2 g | isoproturon, 99.0% |
| 101.7 g | fluoroglycofen-ethyl, 88.5% |
| 427.5 g | ® Genamin Reserve C |
| 189.0 g | ® Genapol Pf 40 |
| 54.0 g | Hoe S 3775 (Hoechst AG) |
| 52.7 g | ® Luviskol K30 |
| 22.5 g | defoamer SE2 (93.7 g of 24% aqueous dispersion are employed) |
| 200.2 g | ® Wessalon S |
| 4456.8 g | water |
| 8913.6 g | |

The components are first precomminuted in a suitable manner and then mixed and ground on a bead mill until 50% of the particles have a size of 2–3 μm.

Granules of the following composition are prepared with this aqueous dispersion as described in Example 1.

| | |
|---|---|
| 75.76% by weight of | isoproturon, 99.0% |
| 2.26% by weight of | fluoroglycofen-ethyl, 88.5% |

-continued

| | |
|---|---|
| 9.50% by weight of | ® Rapidamin Reserve C |
| 4.20% by weight of | ® Genapol Pf40 |
| 1.20% by weight of | Hoe S 3775 (Hoechst AG) |
| 1.17% by weight of | ® Luviskol K30 |
| 0.50% by weight of | defoamer SE2 |
| 4.45% by weight of | ® Wessalon S |
| 0.96% by weight of | residual moisture |
| 100.00% by weight | |

Biological activity of the products prepared in Examples 1 to 4

| | Isoproturon + fluoroglycofen-ethyl g/ai/ha | Activity in % | | | | | | |
|---|---|---|---|---|---|---|---|---|
| | | STEME | GALAP | VERHE | VIOAR | LAMAM | TRZAS | HORVS |
| Ex. 1 | 300 + 7.5 | 100 | 88 | 68 | 78 | 65 | 0 | 3 |
| | 600 + 15 | 100 | 92 | 85 | 94 | 83 | 0 | 7 |
| Ex. 2 | 300 + 7.5 | 100 | 78 | 80 | 90 | 70 | 0 | 4 |
| | 600 + 15 | 100 | 92 | 88 | 96 | 83 | 0 | 6 |
| Ex. 3 | 300 + 7.5 | 99 | 83 | 88 | 88 | 93 | 0 | 4 |
| | 600 + 15 | 100 | 89 | 94 | 94 | 95 | 0 | 6 |
| Ex. 4 | 300 + 7.5 | 75 | 15 | 54 | 54 | 14 | 0 | 2 |
| | 600 + 15 | 86 | 32 | 69 | 65 | 30 | 0 | 5 |

Key:
STEME = *Stellaria media*
GALAP = *Galium aparine*
VERHE = *Veronica heterifolia*
VIOAR = *Viola arvensis*
LAMAM = *Lamium amplexicaule*
TRZAS = spring wheat
HORVS = spring barley The test plants were grown in pots and treated with the test products which had been dissolved in 300 l of water per ha in stage 25–31 (dicots) and in stage 21–25 (monocots). They were scored after 3 weeks.

These examples demonstrate that the biological activity is considerably inferior when fluoroglycofen is not in dissolved form (Example 4).

What is claimed is:

1. Water-dispersible granules of suspoemulsions consisting essentially of
   10 to 90% by weight of one or more pesticidally active substance as the main component, said active substance having a melting point of more than 65° C., which can be formulated in the form of an aqueous dispersion,
   0.1 to 20% by weight of one or more liquid pesticidally active substance or a pesticidally active substance having a melting point below 65° C. and/or which is not sufficiently active in the solid state, in dissolved form,
   0.2 to 20% by weight of a solvent or solvent mixture with a boiling point above 170° C.,
   1 to 12% by weight of one or more wetting agents,
   2 to 15% by weight of one or more dispersants,
   0.2 to 5% by weight of one or more adhesives,
   0.5 to 80% by weight of inert substance and
   0.5 to 10% by weight of one or more emulsifiers.

2. Water-dispersible granules of suspoemulsions consisting essentially of 10 to 90% by weight of isoproturon, which can be formulated in the form of an aqueous dispersion, 0.1 to 20% by weight of fluoroglycofen-ethyl, in dissolved form, 0.2 to 20% by weight of a solvent or solvent mixture with a boiling point above 170° C., 1 to 12% by weight of one or more wetting agents, 2 to 15% by weight of one or more dispersants, 0.2 to 5% by weight of one or more adhesives, 0.5 to 80% by weight of inert substance and 0.5 to 10% by weight of one or more emulsifiers.

3. Water-dispersible granules of suspoemulsions consisting essentially of 10 to 90% by weight of endosulfan, which can be formulated in the form of an aqueous dispersion, 0.1 to 20% by weight of deltamethrin, in dissolved form, 0.2 to 20% by weight of a solvent or solvent mixture with a boiling point above 170° C., 1 to 12% by weight of one or more wetting agents, 2 to 15% by weight of one or more dispersants, 0.2 to 5% by weight of one or more adhesives, 0.5 to 80% by weight of inert substance and 0.5 to 10% by weight of one or more emulsifiers.

4. The granules as claimed in claim 1, further comprising at least one safener.

5. The method for controlling undesired plant growth, which comprises applying a preparation which contains a herbicidal agent as claimed in claim 1 in the form of an aqueous preparation to plants, seeds of plants or the area under cultivation.

6. The method for controlling undesired pests, which comprises applying a preparation as claimed in claim 1, in the form of an aqueous preparation to plants, seeds of plants or the area under cultivation.

* * * * *